United States Patent [19]

Nickson

[11] 4,182,337
[45] Jan. 8, 1980

[54] SURGICAL INSTRUMENT FOR PERFORMING EMERGENCY TRACHEOTOMIES

[76] Inventor: Kenneth L. Nickson, 2180 Gainsborough Dr., Riverside, Calif. 92506

[21] Appl. No.: 830,848

[22] Filed: Sep. 6, 1977

[51] Int. Cl.² .............................................. A61B 17/32
[52] U.S. Cl. .................................. 128/305.3; 128/351
[58] Field of Search ...................... 128/305, 305.3, 307, 128/309, 317, 305.1, 2 B, 351; 32/48, 49; 30/388, 389, 276, 185, 272 R, 263

[56] References Cited

U.S. PATENT DOCUMENTS

| 1,692,148 | 11/1928 | Arnold | 46/48 |
| 3,991,765 | 11/1976 | Cohen | 128/305 |

FOREIGN PATENT DOCUMENTS

| 3584 | 1/1835 | France | 32/48 |

Primary Examiner—Robert W. Michell
Assistant Examiner—Michael H. Thaler
Attorney, Agent, or Firm—Christie, Parker & Hale

[57] ABSTRACT

A surgical instrument for performing emergency tracheotomies comprises a rigid body having a circular cutter at one end used to make an incision in the front of the neck and in the trachea. The rigid body has a pair of fixed supports on opposite sides for supporting the fingers of the user, while a third movable support slides forward under thumb-pressure to move an actuating rod which, in turn, operates a gear mechanism for rotating the cutter blade during the incision. The rigid body can be held in one hand while the other hand is used to locate the area of the neck where the incision should be made. The undersurface of the rigid body is shaped as an elongated groove which conforms to the configuration of a trachea tube and provides a guide for inserting the trachea tube through the opening provided by the incision.

21 Claims, 7 Drawing Figures

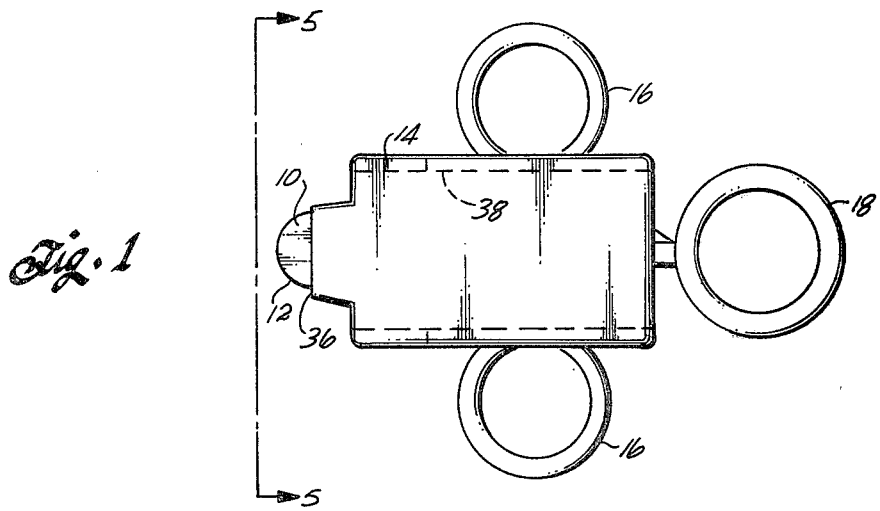
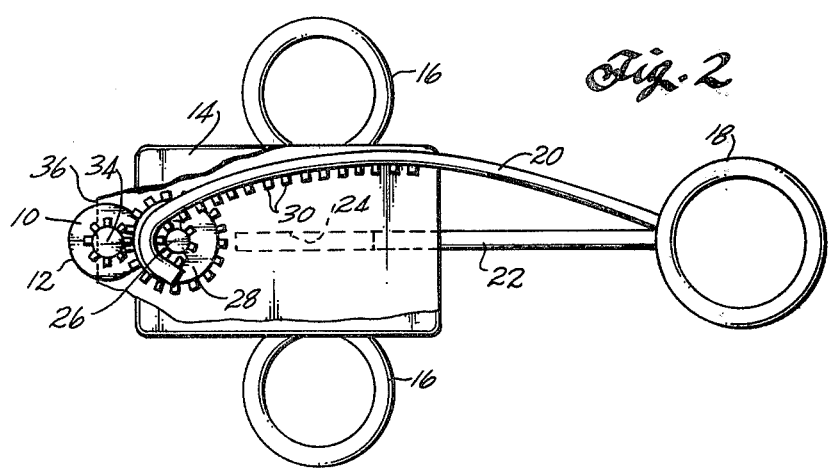
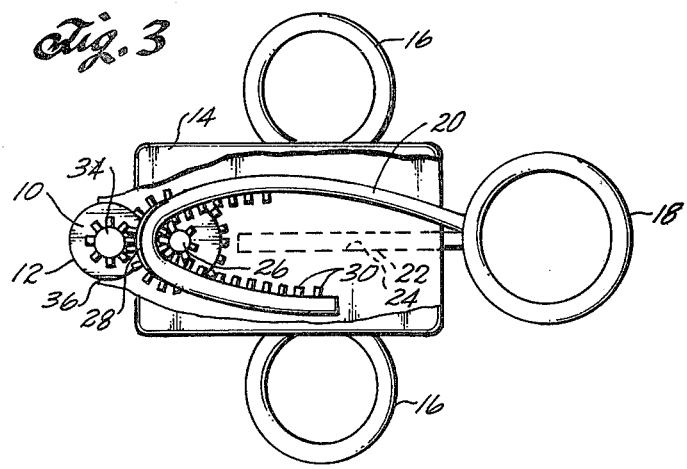

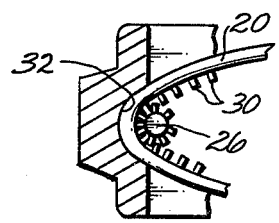
Fig. 4
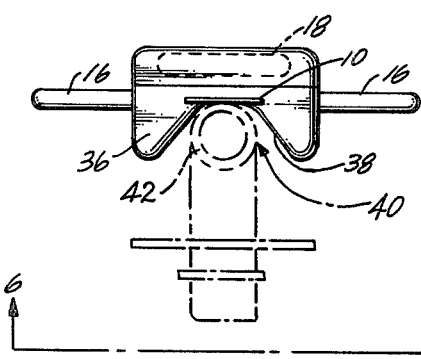
Fig. 5
Fig. 6
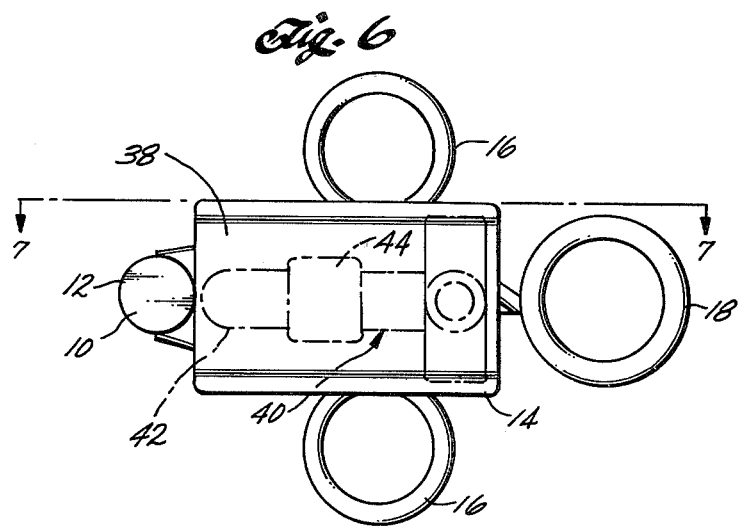
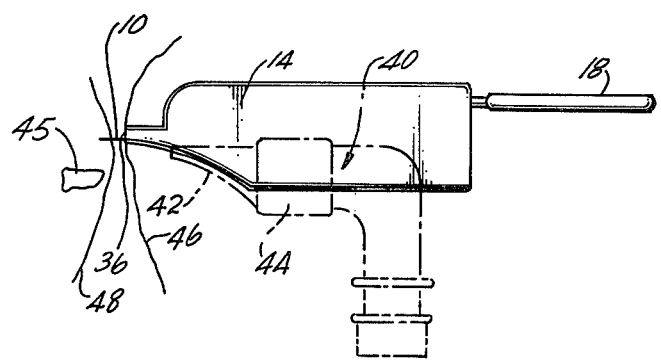
Fig. 7

SURGICAL INSTRUMENT FOR PERFORMING EMERGENCY TRACHEOTOMIES

BACKGROUND OF THE INVENTION

This invention relates to a surgical instrument for performing emergency tracheotomies.

A tracheotomy is an operation for the purpose of relieving an obstruction in the respiratory passage. The instrument provided by this invention is used to make an incision in the front of the neck and in the trachea in preparation for inserting a tracheotomy tube through the incision and into the trachea. The tracheotomy tube provides an emergency airway to the trachea for allowing the patient to breathe.

A number of surgical instruments for performing tracheotomies have been disclosed in the following patents:

| U.S. Pat. No. | Patentee |
| --- | --- |
| 300,285 | Russell |
| 2,991,787 | Shelden et al |
| 3,688,773 | Weiss |
| 3,759,263 | Taylor |
| 3,817,250 | Weiss et al |
| 3,886,946 | Hyde |

These instruments use a needle or a blade having a pointed end which is positioned over the patient's throat and pushed forward to puncture an incision through the tissues in the throat area and the trachea. Extreme care must be used to ensure that the incision into the trachea is made immediately and accurately, while ensuring that too much pressure is not applied which could result in the puncturing needle or blade passing through the opposite side of the trachea, for example. The puncture is made in a hollow area of the throat where it can be difficult to accurately limit the pressure applied when puncturing an opening in such a hollow area, especially when the depth of the puncture should not exceed about ½-inch.

The present invention provides a surgical instrument which does not puncture an opening, but rather makes a narrow, slit-type incision from a cutter blade which moves laterally while being pushed forward into the trachea. In this way, the incision can be made safer because it requires less forward pressure to make the incision than with a puncturing instrument. By making an incision with less pressure applied to the incision-making instrument, the physician or technician has better control over the depth of the incision, and hence the incision is more accurate. Moreover, the incision made by the instrument of this invention does not nearly cause the amount of tissue damage resulting from an incision made with a puncturing instrument.

SUMMARY OF THE INVENTION

Briefly, the surgical instrument provided by this invention comprises an elongated rigid body having a rotatable cutter with a rounded blade edge at one end of the rigid body. A blade-actuating member slidably secured to the rigid body rotates the cutter in response to sliding movement relative to the rigid body. The rigid body can be held in one hand while the other hand is used to locate the area where the incision should be made. The actuating member then can be pushed forward under thumb-pressure to rotate the cutter on its axis so that the cutter will be drawn laterally across the tissues in the throat area and the trachea to make a slit-type incision while being pushed forward under the thumb-pressure applied to the actuating member. In this way, less pressure is required to make the incision than with a puncturing instrument. The incision made by the present invention also produces much less tissue damage in the area of the incision because of the reduced pressure applied to the instrument.

The present invention also includes means for limiting the depth of the incision to a selected distance, and means for guiding a tracheotomy tube into the opening provided by the incision.

These and other aspects of the invention will be more fully understood by referring to the following detailed description and the accompanying drawings.

DRAWINGS

FIG. 1 is a top plan view showing a surgical instrument according to principles of this invention;

FIG. 2 is a bottom plan view, partly broken away, showing a mechanism for rotating a cutter blade on the instrument shown in FIG. 1;

FIG. 3 is a bottom plan view, partly broken away, similar to that of FIG. 2 showing the cutter-rotating mechanism in a different position;

FIG. 4 is a fragmentary, cross-sectional bottom plan view showing one aspect of the cutter-rotating mechanism;

FIG. 5 is a front elevation view taken on line 5—5 of FIG. 1;

FIG. 6 is a bottom plan view taken on line 6—6 of FIG. 5; and

FIG. 7 is a side elevational view taken on line 7—7 of FIG. 6.

DETAILED DESCRIPTION

Referring to FIG. 1, a surgical instrument includes a rotatable cutter 10 for making an incision in preparation for performing an emergency tracheotomy. The cutter 10 comprises a flat circular blade having blade edge 12 extending around the periphery of the cutter. The cutter rotates about an upright axis at one end of a rigid body 14 which houses a mechanism for rotating the cutter 10. The rigid body has a longitudinal axis and the cutter 10 is located on the longitudinal axis of the rigid body.

A pair of rings 16 are rigidly affixed to opposite sides of the rigid body 14. The rings are adapted to accommodate two of the fingers of the user of the instrument, providing a means of support for holding the rigid body in one hand during use. A third ring 18 is movably secured to the end of the rigid body 14 opposite the cutter 10. The movable ring 18 accommodates the thumb of the user which can be moved axially in and out toward and away from the rigid body to actuate the mechanism for rotating the cutter 10.

The cutter-rotating mechanism is shown in FIGS. 2 through 4. It comprises an actuating member 20 which slides in and out along a path extending generally longitudinally with respect to the longitudinal axis of the rigid body. A rigid guide member 22 slides longitudinally in an elongated bore 24 extending along the longitudinal axis of the rigid body. The guide member 22 is offset vertically from the actuating member, and the actuating member is spaced apart laterally from the guide member. The rigid guide member 22 is secured to the movable ring 18 and provides a means for guiding the longitudinal sliding travel of the actuating member 20. The actuating member 20 travels along a path which, for the most part, extends longitudinally and generally parallel to the guide member 22. The actuating member 20 is flexible laterally and its front portion actually travels in an arcuate path shown in FIGS. 2 and 3.

The actuating member 20 is engaged with a first gear 26 which rotates about a vertical axis inboard from the cutter 10. The first gear 26 rotates in unison about a common axis with a larger second gear 28. The actuating member 20 has spaced apart gear teeth 30 arranged serially along its inside edge. The flexibility of the actuating member allows its gear teeth 30 to follow a circularly-curved path while engaging gear teeth on the smaller first gear 26. The outside edge of the flexible actuating member engages a ciruclarly-curved guide surface 32, shown in FIG. 4, which guides the arcuate travel of the actuating member 20 and holds the actuating member in engagement with the gear teeth of the first gear 26.

A third rotating gear 34 rotates with the cutter 10 about a common axis. The third gear 34 is engaged with the second gear 28 so that rotation of the first and second gears rotates the third gear which, in turn, rotates the cutter 10 about its axis.

Thus, inward thumb-pressure exerted on the ring 18 moves the actuating member 20 longitudinally inwardly while being guided by the axial travel of the guide member 22. The curved innermost portion of the flexible actuating member 20 converts the generally longitudinal sliding travel of the actuating member into rotary movement of the circular cutter 10. The actuating member 20 in its full outwardly extended position is shown in FIG. 2; and FIG. 3 shows the actuating member 20 at the end of its inward stroke.

Alternatively, the cutter-rotating mechanism can be a rack and pinion device in which forward thumb-pressure moves an elongated rack longitudinally which, in turn, rotates a pinion gear engaged with a gear for rotating the cutter blade.

The cutter 10 projects away from a flat leading edge 36 of the rigid body 14. The cutter 10 projects longitudinally away from the edge 36 by a distance of about ½-inch, which is the depth of a typical incision for a tracheotomy, although this distance can vary in the instrument depending upon whether the instrument is for pediatric or adult use, for example. The flat leading edge 36 projects beyond opposite sides of the cutter as well as above the cutter to provide a stop to limit the desired depth of the incision during use.

The undersurface of the rigid body is shaped as a downwardly-facing, generally U-shaped elongated groove 38 which extends from one end of the body to the other. The top of the groove is shaped to the curvature of a tracheotomy tube 40 shown in phantom lines in FIGS. 5 through 7. The top of the groove is substantially in the same plane as the cutter 10; and as shown in FIG. 5, the cutter is essentially tangent to the curved upper extremity of the groove 38. The tracheotomy tube used with the surgical instrument of this invention has a front end with a beveled, downwardly-facing undersurface 42. A conventional inflatable seal 44 is spaced to the rear of the beveled or tapered tip 42 of the tracheotomy tube.

In using the surgical instrument of this invention, the rigid body 14 is held in one hand by inserting the fingers through the fixed rings 16 on opposite sides of the rigid body. The other hand is used to locate the area where the incision is to be made. Referring to FIG. 7, the incision is preferably made by locating the cricoid cartiledge 45 in the patient's neck by depressing the skin 46 along the front of the neck or in the throat area. The incision is then made just above the cricoid cartiledge 45 in an area where the skin is relatively thin, so that only a shallow incision need be made. The area just above the cricoid cartiledge is probably the safest area for such an incision. The thumb is then inserted in the movable ring 18 and the actuating member 20 is pushed forward in the direction of the cutter to rotate the cutter 10. The instrument is pushed forward against the throat area while the thumb is being pushed forward to continuously rotate the cutter 10 during forward travel to form a narrow incision through the tissues in the throat area and into the trachea 48. The leading edge 36 finally comes into contact with the skin 36 to limit the depth of the incision into the trachea. The rigid body 14 is held in place after the incision is made, and the tracheotomy tube 40 is pushed forward into the incision, using the curved undersurface of the groove 38 as a guide. The tapered tip 42 of the tracheotomy tube 40 is pushed forward into the incision while the cutter blade 10 is removed to insert the tube 40 in the incision formed in the trachea 46. Following insertion of the tracheotomy tube, the seal 44 is inflated in the opening in the neck so that air will flow through the tube and not around it.

Thus, the invention provides a surgical instrument with a flat, circular rotatable cutter which can be rotated on its axis so that it forms a narrow, elongated incision by, in effect, drawing the blade laterally across the surface of the tissues of the throat area and trachea while the cutter is being pushed longitudinally into the trachea. This reduces the amount of longitudinal force required to make the incision when compared with instruments shaped as a needle or pointed blade edge. Such instruments require puncturing the skin and therefore more applied pressure to make the required incision. The depth of the incision is of critical importance and is much easier to control with the smaller amount of force required by the instrument of this invention. By reducing the amount of force required for the incision, the present invention provides a safer incision as well as reducing the amount of tissue damage in the area of the incision.

I claim:

1. A surgical instrument for performing emergency tracheotomies comprising an elongated rigid body; a cutter having a rounded blade edge rotatably secured to one end of the rigid body; blade-actuating means slidably secured to the body for rotating the cutter on its axis in response to sliding movement of the blade-actuating means relative to the body; an elongated groove formed in an undersurface of the rigid body, the groove being aligned longitudinally with the cutter; and a trachea tube adapted to slide in the groove toward and under the cutter.

2. Apparatus according to claim 1 in which the groove extends lengthwise toward an edge of the body; and the cutter is rotatable at the edge of the body.

3. Apparatus according to claim 2 in which the cutter is rotatable in a plane substantially tangent to the top of the groove.

4. Apparatus according to claim 2 in which the blade-actuating means comprises a slidable blade-actuating member and means for moving the slide member longitudinally relative to the body toward the cutter; and means for converting such linear travel of the member into rotation of the cutter.

5. Apparatus according to claim 4 in which the cutter is rotatable in a plane substantially tangent to the top of the groove.

6. Apparatus according to claim 1 including stop means on the rigid body for limiting penetration of the cutter into the skin.

7. Apparatus according to claim 1 in which the blade-actuating means comprises a slide member projecting from the body on an end thereof opposite the cutter; and including means for moving the slide member toward the cutter to rotate the cutter about its axis.

8. Apparatus according to claim 7 including means engaged with the slide member for converting linear travel of the slide member into rotatable movement of the cutter.

9. Apparatus according to claim 8 in which said means for converting linear travel into rotation of the cutter comprises first gear means secured to the cutter, second gear means to rotate the first gear means, and in which substantially linear travel of the slide member rotates the second gear means.

10. Apparatus according to claim 9 in which the slide member comprises a flexible member having a first portion which can travel in an arcuate path in contact with the second rotatable gear means when a second portion of the flexible member is moved linearly.

11. Apparatus according to claim 10 including means for providing guided linear movement of said second portion of the flexible member.

12. Apparatus according to claim 7 including means on opposite sides of the body for supporting the fingers of the instrument user; and in which the blade-actuating member includes means for supporting the thumb of the user at an end of the body opposite the cutter.

13. Apparatus according to claim 1 in which the blade-actuating means comprises a slidable blade-actuating member and means for moving the slide member longitudinally relative to the body toward the cutter; and means for converting such linear travel of the member into rotation of the cutter.

14. Apparatus according to claim 13 including stop means on the rigid body for limiting penetration of the cutter into the skin.

15. Apparatus according to claim 1 in which the trachea tube has a tapered front end.

16. Apparatus according to claim 1 in which the trachea tube has a front end with a downwardly-facing taper.

17. A surgical instrument for performing emergency tracheotomies comprising a rigid body, a cutter having a rounded blade edge projecting from the rigid body, means for allowing rotation of the cutter on its axis, blade-actuating means engaged with the cutter rotating means to rotate the cutter on its axis, an elongated inverted U-shaped groove aligned with the cutter and extending along an undersurface of the body, and a trachea tube adapted to slide in the groove toward and under the cutter.

18. Apparatus according to claim 17 in which the cutter is rotatable in a plane substantially tangent to the top of the groove.

19. Apparatus according to claim 18 including stop means on the rigid body for limiting penetration of the cutter into the skin.

20. Apparatus according to claim 17 in which the rigid body is adapted to be held in one hand and the cutter-actuating means is adapted to be actuated by such one hand to rotate the cutter on its axis.

21. Apparatus according to claim 17 including means adapted for engagement with two fingers of a hand of a user for holding the rigid body, and means for being actuated with the thumb of the same hand for rotating the cutter on its axis.

* * * * *

UNITED STATES PATENT AND TRADEMARK OFFICE
CERTIFICATE OF CORRECTION

PATENT NO. : 4,182,337
DATED : January 8, 1980
INVENTOR(S) : Kenneth L. Nickson

It is certified that error appears in the above-identified patent and that said Letters Patent are hereby corrected as shown below:

Column 6, line 26, change "18" to -- 17 --.

Signed and Sealed this

Fifth Day of August 1980

[SEAL]

Attest:

SIDNEY A. DIAMOND

Attesting Officer

Commissioner of Patents and Trademarks